US012042281B2

(12) United States Patent
Grant (10) Patent No.: US 12,042,281 B2
(45) Date of Patent: Jul. 23, 2024

(54) FLUORESCENT NANOMATERIAL SENSORS AND RELATED METHODS

(71) Applicant: Terumo Cardiovascular Systems Corporation, Ann Arbor, MI (US)

(72) Inventor: Christopher F. Grant, South Lyon, MI (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 961 days.

(21) Appl. No.: 16/514,630

(22) Filed: Jul. 17, 2019

(65) Prior Publication Data

US 2021/0015410 A1     Jan. 21, 2021

(51) Int. Cl.
| | |
|---|---|
| *A61B 5/1455* | (2006.01) |
| *G01N 21/64* | (2006.01) |
| *G01N 21/71* | (2006.01) |
| *B82Y 20/00* | (2011.01) |
| *B82Y 40/00* | (2011.01) |
| *G01N 21/77* | (2006.01) |

(52) U.S. Cl.
CPC ...... *A61B 5/14552* (2013.01); *A61B 5/14556* (2013.01); *G01N 21/6428* (2013.01); *G01N 21/648* (2013.01); *G01N 21/71* (2013.01); *B82Y 20/00* (2013.01); *B82Y 40/00* (2013.01); *G01N 2021/6432* (2013.01); *G01N 2021/6441* (2013.01); *G01N 2021/7786* (2013.01)

(58) Field of Classification Search
CPC ............ A61B 5/14552; A61B 5/14556; G01N 21/6428; G01N 21/648; G01N 21/71; G01N 2021/6432; G01N 2021/6441; G01N 2021/7786; G01N 21/6489; G01N 33/521; B82Y 20/00; B82Y 15/00; B82Y 40/00

See application file for complete search history.

(56) References Cited

U.S. PATENT DOCUMENTS

| | | | | |
|---|---|---|---|---|
| 5,997,818 | A | * | 12/1999 | Hacker .............. A61B 5/14557 422/68.1 |
| 6,009,339 | A | * | 12/1999 | Bentsen ............. A61B 5/14557 600/322 |

(Continued)

FOREIGN PATENT DOCUMENTS

| | | |
|---|---|---|
| EP | 1496126 | 8/2005 |
| GB | 2554920 | 4/2018 |

(Continued)

OTHER PUBLICATIONS

Rolfe, P. "Micro- and Nanosensors for Medical and Biological Measurement", Sensors and Materials, vol. 24, No. 6 (2012) 275-302.

(Continued)

*Primary Examiner* — Ioleta A Prieto
(74) *Attorney, Agent, or Firm* — Fish & Richardson P.C.

(57) ABSTRACT

Sensors can be used for the detection of an analyte concentration, such as an electrolyte and/or a blood gas. In some embodiments, such sensors can include a matrix material, a nanoparticle associated with the matrix material, and a signaling molecule associated with the nanoparticle. In particular embodiments, the signaling molecule can exhibit a fluorescence emission intensity as a function of the analyte concentration.

25 Claims, 2 Drawing Sheets

(56) References Cited

U.S. PATENT DOCUMENTS

| | | | |
|---|---|---|---|
| 6,051,437 A * | 4/2000 | Luo | B82Y 30/00 436/172 |
| 6,101,406 A * | 8/2000 | Hacker | A61B 5/14557 422/68.1 |
| 6,208,880 B1 * | 3/2001 | Bentsen | G01N 21/05 422/68.1 |
| 6,268,222 B1 | 7/2001 | Chandler et al. | |
| 6,383,767 B1 | 5/2002 | Polak | |
| 6,454,710 B1 | 9/2002 | Ballerstadt et al. | |
| 6,773,926 B1 | 8/2004 | Freund et al. | |
| 7,521,019 B2 | 4/2009 | Polak et al. | |
| 7,613,504 B2 | 11/2009 | Rowe | |
| 7,809,441 B2 * | 10/2010 | Kane | A61N 1/37288 607/22 |
| 8,216,854 B2 | 7/2012 | Ballerstadt et al. | |
| 8,409,877 B2 | 4/2013 | Liu et al. | |
| 8,498,682 B2 | 7/2013 | Markle et al. | |
| 9,276,063 B2 | 3/2016 | Zhang et al. | |
| 9,309,550 B2 | 4/2016 | Cooper et al. | |
| 9,625,456 B2 | 4/2017 | Bradbury et al. | |
| 9,901,295 B2 | 2/2018 | Iverson et al. | |
| 2002/0160520 A1 | 10/2002 | Orloff | |
| 2005/0027176 A1 | 2/2005 | Xie | |
| 2005/0096516 A1 * | 5/2005 | Soykan | G01N 21/6428 600/317 |
| 2005/0148100 A1 | 7/2005 | Su et al. | |
| 2007/0105176 A1 | 5/2007 | Ibey et al. | |
| 2007/0208243 A1 | 9/2007 | Gabriel et al. | |
| 2007/0270674 A1 * | 11/2007 | Kane | A61N 1/36557 604/20 |
| 2007/0270675 A1 * | 11/2007 | Kane | A61N 1/3962 600/315 |
| 2008/0039816 A1 | 2/2008 | Svarovsky et al. | |
| 2009/0118605 A1 | 5/2009 | Van Duyne et al. | |
| 2009/0305291 A1 * | 12/2009 | Pompa | C12Q 1/6834 435/7.1 |
| 2010/0254911 A1 | 10/2010 | Sharma et al. | |
| 2010/0279428 A1 | 11/2010 | Rhee et al. | |
| 2011/0105866 A1 | 5/2011 | Markle et al. | |
| 2011/0152658 A1 | 6/2011 | Peyser et al. | |
| 2011/0275985 A1 | 11/2011 | Lowery, Jr. et al. | |
| 2012/0088258 A1 | 4/2012 | Bishop et al. | |
| 2012/0197231 A1 * | 8/2012 | Kane | A61B 5/14546 607/18 |
| 2013/0197327 A1 | 8/2013 | Chen et al. | |
| 2014/0246624 A1 | 9/2014 | Seubert et al. | |
| 2015/0030544 A1 * | 1/2015 | Clark | G01N 33/582 435/14 |
| 2016/0243262 A1 | 8/2016 | Ortac et al. | |
| 2016/0258964 A1 | 9/2016 | Zhang et al. | |
| 2017/0173262 A1 | 6/2017 | Veltz | |
| 2017/0212124 A1 | 7/2017 | Thalhammer et al. | |
| 2017/0340225 A1 | 11/2017 | Ulmer et al. | |
| 2018/0055426 A1 * | 3/2018 | Kane | A61B 5/14546 |
| 2019/0167112 A1 * | 6/2019 | Kane | G01N 21/78 |
| 2019/0167162 A1 * | 6/2019 | Li | A61B 5/1459 |
| 2019/0284601 A1 * | 9/2019 | Chiu | G01N 21/64 |
| 2020/0003765 A1 * | 1/2020 | Chowdhury | G01N 33/582 |

FOREIGN PATENT DOCUMENTS

| | | |
|---|---|---|
| JP | 2004-529352 | 9/2004 |
| JP | 2005-151972 | 6/2005 |
| JP | 2008-545980 | 12/2008 |
| JP | 2010-526599 | 6/2011 |
| JP | 2018-513352 | 5/2018 |
| WO | WO 2000/12536 | 3/2000 |
| WO | WO 2002/054076 | 7/2002 |
| WO | WO 2005/043157 | 5/2005 |
| WO | WO 2008/072209 | 6/2008 |
| WO | WO 2008/091792 | 7/2008 |
| WO | WO 2013/134401 | 9/2013 |
| WO | 2017/214047 | 12/2017 |
| WO | WO 2017/210841 | 12/2017 |

OTHER PUBLICATIONS

Wang et al., "Electrochemical Sensors for Clinic Analysis", Sensors (2008), 8, 2043-2081.

Wolfbeis, O.S.., "An overview of nanoparticles commonly used in fluorescent bioimaging", The Royal Society of Chemisty, Chem Soc Rev (2015) 44, 4743-4768.

Xue, R., Dissertion, "Nanofiber Based Optical Sensors for Oxygen Determination", The Ohio State University (2014) 206 pages.

Cheng-Shane et al., "Fluorescence Ratiometric Optical Broad Range pH Sensor Based on CdSe/ZnS Quantum Dots and 0170 Embedded in Ethyl Cellulose Matrix," Journal of Lightwave Technology, 2018, 36(4): 857-862, 6 pages.

GB Office Action in United Kingdom Appln. No. 2009889.3, dated Mar. 3, 2021, 3 pages.

GB Office Action in United Kingdom Appln. No. 2009889.3, dated Dec. 4, 2020, 4 pages.

Kurabayashi et al., "CdSe/ZnS Quantum Dots Conjugated with a Fluorescein Derivatives: a FRET-based pH Sensor for Physiological Alkaline Conditions," Analytical Science, May 10, 2014, vol. 30, 6 pages.

Office Action in Japanese Appln. No. 2020-121195, dated Jan. 16, 2024, 19 pages (with English translation).

\* cited by examiner

FLUORESCENT NANOMATERIAL SENSORS AND RELATED METHODS

BACKGROUND

Technical Field

The present disclosure relates to sensors used to detect and measure analyte concentrations, and more particularly to fluorescent nanomaterial sensors used to detect, measure, and monitor biological analytes.

Background Information

Monitoring of biological analytes such as pH, blood gases, electrolytes, and metabolites has been one of the primary avenues to assess the general health of individuals and the status of their bodily functions, especially in critical-care settings. For example, dedicated analyzers are used in near-patient testing environments to provide for continuous, real time measurement and detection of blood analytes during critical care situations. Measurement of blood analytes provide valuable information regarding the state of oxygenation, gas exchange, acid-base homeostasis, and ventilation of an individual. Though various biological analyte sensor technologies have been developed, improvements in design, functionality, and accuracy are continually sought.

SUMMARY

The present disclosure describes sensors used to detect and measure analyte concentrations, and more particularly to fluorescent nanomaterial sensors used to detect, measure, and monitor blood gas analytes.

In one aspect, this disclosure is directed to a sensor for the detection of an analyte concentration. The sensor includes a matrix material, a nanoparticle associated with the matrix material, and a signaling molecule associated with the nanoparticle. The nanoparticle or the signaling molecule exhibits a fluorescence emission intensity as a function of the analyte concentration.

Such a sensor may optionally include one or more of the following features. The analyte may be potassium, oxygen, carbon dioxide, a hydrogen ion, or any combination thereof. The matrix material may be a hydrogel matrix. The matrix material may be permeable to the analyte. The nanoparticle may be a polymeric nanoparticle. The nanoparticle may be a quantum dot. The quantum dot may exhibit a distinguishable emission wavelength. The signaling molecule may alter a fluorescence emission intensity of the quantum dot as a function of the analyte concentration. The signaling molecule may decrease or increase the fluorescence emission intensity of the nanoparticle in the absence of the analyte. The signaling molecule may increase or decrease the fluorescence emission intensity of the nanoparticle in the presence of the analyte. The signaling molecule may be a fluorophore. The signaling molecule may be a non-fluorophore molecule. The signaling molecule may be hydroxypyrenetrisulfonic acid, benzo[ghi]perylene, a coumarocryptand, or any combinations thereof. The sensor may be optically coupled to a measuring device. The sensor may be a ratiometric sensor. The nanoparticle or the signaling molecule may exhibit a fluorescence emission intensity as a function of a temperature.

In another aspect, this disclosure is directed to a sensor for the detection of an analyte concentration that includes a matrix material, a donor chromophore, and an acceptor chromophore. The donor chromophore may transfer energy to the acceptor chromophore in the presence of the analyte, causing the acceptor chromophore to exhibit a distinguishable emission wavelength indicative of the presence of the analyte.

Such a sensor may optionally include one or more of the following features. The analyte may be potassium, oxygen, carbon dioxide, a hydrogen ion, or any combination thereof. The matrix material may be a hydrogel matrix. The matrix material may be permeable to the analyte. The donor chromophore or the acceptor chromophore may be a nanoparticle. The nanoparticle may be a polymeric nanoparticle. They nanoparticle may be a quantum dot. The acceptor chromophore or the donor chromophore may be a fluorescent dye. The sensor may be optically coupled to a measuring device. The sensor may be a ratiometric sensor. The donor chromophore may transfer energy to the acceptor chromophore as a function of a temperature, causing the acceptor chromophore to exhibit a distinguishable emission wavelength indicative of a temperature change.

In yet another aspect, this disclosure is directed to a method of detecting an analyte concentration in a fluid. The method includes providing one or more sensors that include a matrix material, a nanoparticle associated with the matrix material, and a signaling molecule associated with the nanoparticle. The signaling molecule or the nanoparticle may exhibit a fluorescence emission intensity that depends on the analyte concentration. The method may also include exposing the one or more sensors to the fluid. The method may also include measuring the fluorescence emission intensity. The method may also include detecting the analyte based on the measured fluorescence intensity.

Such a method may optionally include one or more of the following features. The fluid may be a biological fluid. The biological fluid may be blood.

Particular embodiments of the subject matter described in this document can be implemented to realize one or more of the following advantages. In some embodiments, the sensors provided herein can have increased stability, allowing use beyond about 6 hours. In some cases, such extended stability of the sensors provided herein can be beneficial in critical care situations such as surgery, where it would be preferable to avoid having to re-calibrate, re-prime, and/or exchange a sensor during surgery, as continuous monitoring of a blood analytes in a patient is vital. In addition, the time a clinician takes to exchange, re-calibrate, or re-prime a sensor may be reduced. This, in turn, can lead to a reduced risk of clinician error during a calibration and/or measurement stage using the sensor. Furthermore, the sensors provided herein may have reduced interference and/or noise and consequently, improved accuracy. A reduction in interference and/or noise may result in improved sensitivity, specificity, precision, and/or accuracy of the sensor measurements. Moreover, in some embodiments, the sensors of the disclosure may utilize a single probe (e.g., a nanoparticle) to detect and measure multiple analytes. Such multi-analyte sensors having a single probe may improve manufacturability and quality control. For example, a multi-analyte sensor using multiple probes to detect two or more analytes is typically manufactured using at least two manufacturing processes, corresponding to each probe. The sensors provided herein may be manufactured in a single process; thereby, reducing total manufacturing time and quality control activities (e.g., quality inspections to ensure proper sensor performance).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The use of the term "about," as used herein, refers to an amount that is near the stated amount by about 10%, 5%, or 1%, including increments therein. For example, "about" can mean a range including the particular value and ranging from 10% below that particular value and spanning to 10% above that particular value.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

The present disclosure describes sensors used to detect and measure analyte concentrations, and more particularly to fluorescent nanomaterial sensors used to detect, measure, and monitor blood gas analytes.

Figure 1:
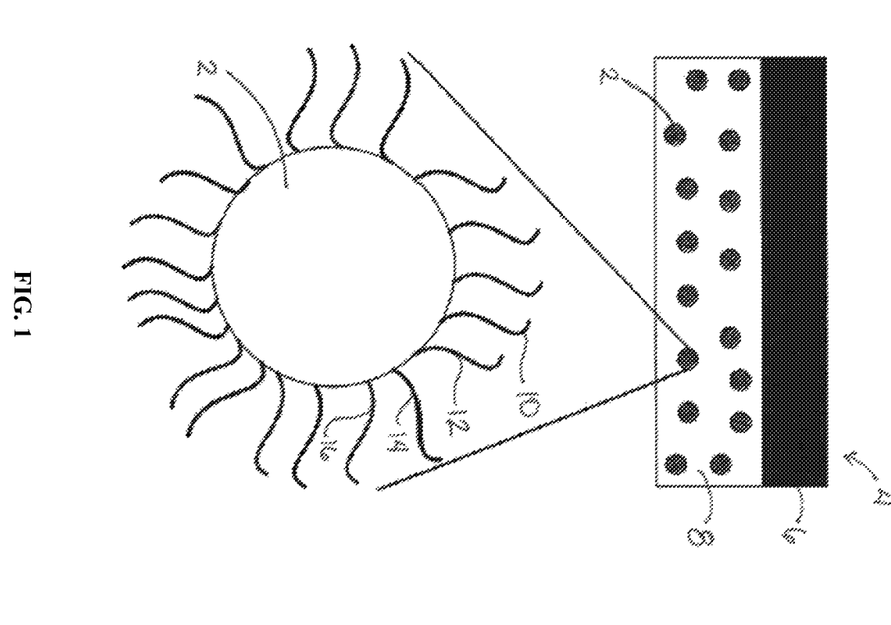
FIG. 1 is a schematic depiction of a sensor in accordance with some embodiments provided herein.

Referring to FIG. 1, an example sensor 4 for the detection of an analyte concentration is schematically depicted. The sensor 4 includes a matrix material. The sensor 4 further includes an overcoat layer 6 and a chemistry layer 8, as shown in FIG. 1. The overcoat layer 6 may be in fluid contact with or otherwise exposed to the medium containing the analyte of interest to be measured. The overcoat layer 6 may comprise the matrix material. In some embodiments, the matrix material is permeable to the analyte of interest. In some examples, the matrix material is insoluble in the medium to be monitored by sensor 4. In some examples, the matrix material is a hydrogel matrix. The term "hydrogel," as used herein, is defined as a three-dimensional macromolecular material comprising a network structure. In some instances, the hydrogel contains a hydrophobic agent. In some cases, the matrix material is a polymeric material. Non-limiting examples of polymeric materials include ion-permeable cellulosic materials, high molecular weight or crosslinked polyvinyl alcohol (PVA), dextran, crosslinked dextran, polyurethanes, quaternized polystyrenes, sulfonated polystyrenes, polyacrylamides, polyhydroxyalkyl acrylates, polyvinyl pyrrolidones, hydrophilic polyamides, polyesters, and any combination thereof. In some examples, the matrix material is cellulose. In some examples, the matrix material is a cellulose hydrogel. In some embodiments, the matrix material is coated onto a substrate. In some implementations, the substrate is shaped as a disc. In some embodiments, the matrix material is shaped as a disc. In some examples, the matrix material is lyophilized. In some embodiments, the matrix materials is produced via a coating process or the like. Manufacturing the sensor of the disclosure via a coating process would significantly reduce manufacturing complexity, variability, and output compared to conventional manufacturing processes.

The overcoat layer 6 comprises an opacifying layer that optically isolates a nanoparticle and/or a signaling molecule in the chemistry layer 8. The overcoat layer 6 may comprise an optically opaque agent. Non-limiting examples of the optically opaque agent include carbon black, carbon-based opaque agents, ferric oxide, and metallic phthalocyanines. In some embodiments the optically opaque agent is substantially uniformly dispersed in the polymer in an amount effective to provide the desired degree of opacity to provide the desired optical isolation. A particularly useful opaque agent is carbon black. The overcoat layer 6 can also be a coating on the chemistry layer 8. For example, overcoat layer 6 can be an ink coating on the chemistry layer 8 applied using a variety of techniques, such as but not limited to, an inkjet technique or an ink-screening technique. In some cases, the overcoat layer 6 can also be a black membrane associated with the chemistry layer 8. In some examples, the overcoat layer 6 comprises carbon black dispersed in a matrix of epoxy-crosslinked dextran.

As shown in FIG. 1, the chemistry layer 8 comprises one or more nanoparticles 2. Chemistry layer 8 is the sensing layer of sensor 4. In other words, chemistry layer 8 comprises the sensing agents that can detect the concentration of an analyte of interest. In this example, the sensing agents are nanoparticle 2 and a signaling molecule. Nanoparticle 2 is associated with the matrix material. For example, nanoparticle 2 may be embedded or entrapped within the matrix material. In some examples, nanoparticle 2 can be dissolved or dispersed throughout the matrix material. In yet another example, nanoparticle 2 can be adsorbed onto an inner and/or outer surface of the matrix material. In other cases, nanoparticle 2 may be reversibly or irreversibly coupled to the matrix material. Nanoparticle 2 may be covalently coupled to the matrix material. Example conjugation chemistries that can be used to couple nanoparticle 2 to the matrix material include, but are not limited to carbodiimides, N-hydroxysuccinimide esters, imidoesters, maleimidies, haloacetyls, pyridyl disulfides, hydrazides, alkoxyamines, aryl azides, diazirines, Staudinger reagent pairs, or any combination thereof. The matrix material of chemistry layer 8 can be the same as those matrix materials previously described.

Nanoparticle 2 may have a diameter ranging from about 1 to 999 nanometers (nm). In some embodiments, nanoparticle 2 is a metal nanocluster, a carbon nanotube, a nanodiamond, a carbon nanodot, or any combination thereof. In some cases, nanoparticle 2 is a quantum dot. The quantum dot structure may comprise a core and a shell. Quantum dots (QDs) are colloidal, semiconductor, brightly luminescent nanocrystals that typically range in diameter from about 1 to about 10 nm in size. Excitons are generated in the nanocrystals upon absorption of light, and electron-hole recombination leads to luminescence. QDs of the disclosure can be synthesized as core/shell structures, where the core nanocrystal is coated with another semiconductor material to protect and improve its optical properties. Example semiconductor materials used in the preparation of (core/shell) QDs include: CdSe/ZnS, CdTe/ZnS, CdTe/CdSe, CdSe/ZnTe, CdSe/ZnSe, CdTe/ZnSe, InAs/ZnSe, InAs/CdSe, InAs/InP, Cu:InP/ZnSe, InAsxPi-x/InP/ZnSe, CdS/ZnSe, CdSe/CdS, ZnSe/CdSe, ZnSe/InP/ZnS, InP/ZnS, InGaP/ZnS, CdSe/CdS/ZnS, or any combination thereof. Exemplary methods to prepare QDs of the disclosure include, but are not limited to: electron beam lithography, focused ion beam technique, etching process, chemical precipitation methods, sol-gel methods, microemulsion, hot-solution decomposition process, vapor-phase method, molecular beam epitaxy, physical vapor deposition, chemical vapor deposition, ultrasonic or microwave irradiation, hydrothermal synthesis, solvothermal synthesis, electrochemical assembly, cluster-seed method, or any combination thereof. Chemical precipitation methods can include nucleation and nanocrystal growth. Sol-gel methods can involve hydrolysis, condensation, and subsequent gel formation.

In some instances, nanoparticle 2 is a polymeric nanoparticle. Polymeric nanoparticles are colloidal particles having a diameter that is less than 1 micron (μm). Polymeric nanoparticles can form two structures: nanospheres and nanocapsules. Nanospheres are nanoparticles having a solid core or a polymeric matrix core. On the other hand, nanocapsules constitute a vesicular structure forming an interior reservoir surrounded by an outer membrane, wherein the reservoir may comprise an oil and/or an aqueous core. Polymeric nanoparticles of the disclosure may be composed of a synthetic polymer. Non-limiting examples of synthetic polymers used to prepare the polymeric nanoparticle include polylactide (PLA), polyglycolide (PGA), poly-lactic-co-glycolic acid (PLGA), polycyanoacrylate, polycaprolactone (PCL), polyethylene glycol (PEG), polystyrene, polyvinyl alcohol (PVA), polyalkylcyanoacrylate, poly(styrene-co-maleic anhydride), . . . Alternatively, polymerics nanoparticles of the disclosure may be composed of a natural polymers. Non-limiting examples of natural polymers include cellulose, chitosan, collagen, gelatin, alginate, albumin, hyaluronic acid, and dextran. Non-limiting example types of cellulose that may be used to prepare the polymeric nanoparticle include cellulose acetate, cellulose triacetate, cellulose propionate, cellulose acetate propionate, cellulose acetate butyrate, nitrocellulose, cellulose sulfate, methyl cellulose, ethyl cellulose, ethyl methyl cellulose, hydroxyethyl cellulose, hydroxypropyl cellulose, hydroxyethyl methyl cellulose, hydroxypropyl methyl cellulose, ethyl hydroxyethyl cellulose, and carboxymethyl cellulose. Additionally, polymeric nanoparticles of the disclosure can be composed of a combination of synthetic and natural polymers. Polymeric nanoparticles may be prepared from a dispersion of preformed polymers. For example, using solvent evaporation, nanoprecipitation, emulsification, salting out method, dialysis, supercritical fluid technology, or any combination thereof. In addition, polymeric nanoparticles can also be prepared via the polymerization of monomers, including, for example, emulsion, miniemulsion, microemulsion, interfacial polymerization, controlled or living radical polymerization, or any combination thereof. Other example methods to prepare a polymeric nanoparticle of the disclosure include: the coacervation of hydrophilic polymers and desolvation. The polymeric nanoparticles may be prepared using one or a combination of one or more of the previously described methods. Polymeric nanoparticles may range in diameter from about 50 to about 200 nm.

Sensor 4 includes a signaling molecule associated with nanoparticle 2. Sensor 4 can include one or more signaling molecules associated with nanoparticle 2. In some embodiments, one signaling molecule is associated with nanoparticle 2. In some examples, two signaling molecules are associated with nanoparticle 2. In some examples, three signaling molecules are associated with nanoparticle 2. In some examples, four signaling molecules are associated with nanoparticle 2. In some examples, five or more signaling molecules are associated with nanoparticle 2. In the example shown in FIG. 1, nanoparticle 2 has its surface decorated with various signaling molecules including: a pH-responsive signaling molecule 10, a potassium-responsive signaling molecule 12, an oxygen-responsive signaling molecule 14, and a carbon dioxide-responsive signaling molecule 16. In some embodiments, the signaling molecule is a non-fluorophore molecule. In some implementations, the sensor comprises a nanoparticle modified with one or more non-fluorophore molecules such that a fluorescence emission intensity from the nanoparticle (including or not including a signaling molecule) is altered in the presence of one or more analytes. In some examples, the one or more non-fluorophore molecules may alter the fluorescence emission intensity of a signaling molecule associated with the nanoparticle.

The signaling molecule can exhibit a fluorescence emission intensity as a function of the analyte concentration. In some embodiments, the signaling molecule can decrease or increase the fluorescence intensity of the nanoparticle in the absence of the analyte. In another example, the signaling molecule can decrease or increase the fluorescence intensity of the nanoparticle in the presence of the analyte. Sensor 4 can be a ratiometric sensor. The ratiometric sensor may continuously output signals (e.g., two fluorescence intensities), but the relative ratio of the signals may change as a function of the analyte concentration. For example, nanoparticle 2 and the signaling molecule may continuously output a first and second fluorescence intensities, respectively, when measured at two or more wavelengths of an emission spectrum or excitation. However, the first or second intensities or both the first and second fluorescence intensities may increase or decrease as a function of the analyte concentration. Thus, the ratio of the first fluorescence intensity to the second fluorescence intensity may be measured to detect changes in an analyte concentration.

For example, the signaling molecule can be associated with a quantum dot exhibiting a distinguishable emission wavelength. The signaling molecule can alter a fluorescence emission intensity of the quantum dot as a function of the analyte concentration. In some embodiments, the signaling molecule is a capping molecule. The capping molecule may be a turn-on fluorescence probe for analyte detection. The capping molecule can decrease the fluorescence emission intensity of the quantum dot, when associated with the quantum dot, in the absence of the analyte, by acting as a hole trapper. The capping molecule, associated with the quantum dot, can form a complex with one or more analytes of interest (e.g., potassium ions, oxygen, carbon dioxide, and/or hydrogen ions), which further alters the energetic position of a highest occupied molecular orbit (HOMO) of the capping molecule. Consequently, the capping molecule (associated with the quantum dot and the analyte of interest) switches to a condition that is unfavorable for an effective hole transfer; thus, the capping molecule no long decreases the fluorescence emission intensity of the quantum dot. In this manner, the capping molecule acts as an on/off switch that increases the fluorescence emission intensity of the quantum dot in the presence of the analyte of interest. In some embodiments, the capping molecule is p-aminothiophenol.

In another example, the capping molecule may alternatively decrease the fluorescence emission intensity of the quantum dot in the presence of the analyte of interest. In the presence of quenching molecules (i.e., an analyte of interest), a fluorescence signal is reduced due to quenching. For example, as the partial pressure of oxygen ($pO_2$) is increased in a sample, there is an increased number of oxygen molecules that can collide with the fluorophores and result in non-radiative decay (i.e., quenching or decreased fluorescence intensity).

In yet another example, the signaling molecule can be associated with a polymeric nanoparticle. One or more signaling molecules may be associated with the polymeric nanoparticle. The fluorescence emission intensity of the signaling molecules can decrease or increase as a response to the presence of the analyte. Alternatively, the emission intensity of the signaling molecules can decrease or increase as a response to the absence of the analyte.

The signaling molecule can be embedded or entrapped within a polymeric nanoparticle. In yet another example, the signaling molecule can be adsorbed onto an inner and/or outer surface of the nanoparticle 2. In other cases, the signaling molecule may be reversibly or irreversibly coupled to nanoparticle 2. The signaling molecule may be covalently coupled to nanoparticle 2. Example conjugation chemistries that can be used to couple the signaling molecule to the matrix material are known to the skilled artisan and include, but are not limited to carbodiimides, N-hydroxysuccinimide esters, imidoesters, maleimidies, haloacetyls, pyridyl disulfides, hydrazides, alkoxyamines, aryl azides, diazirines, Staudinger reagent pairs, or any combination thereof. The signaling molecule may comprise an amine group and the nanoparticle 2 may comprise a carboxylic acid group, amenable to conjugation chemistries (e.g., carbodiimide chemistry). In other examples, the signaling molecule may comprise a carboxylic acid group and the nanoparticle 2 may comprise an amine group, amenable to conjugation chemistries (e.g., carbodiimide chemistry).

Sensor 4 can be modified with multiple functionalities such that it provides a detectable response one or more chemistries (e.g., of pH, oxygen, carbon dioxide, and potassium ions). In this example, sensor 4 would be excited by a single wavelength and emit an independent signal for each chemistry detected. This would allow for the elimination of optics such as light emitting diodes (LEDs) and filters used in conventional detection systems, thereby reducing cost and complexity to the detection system. Additionally, yet another advantage of the sensors of the disclosure, is having a single raw material manufactured and inspected for all chemistries as compared to manufacturing and inspecting multiple raw materials (i.e., one raw material per type of chemistry). Sensor 4 can detect the concentration of a potassium ion, oxygen, carbon dioxide, a hydrogen ion, a hydronium ion, or any combination thereof. Additional analytes that sensor 4 can detect include, but are not limited to glucose, sodium ions, calcium ions, magnesium ions, chloride ions, creatinine, urea, lactate, bicarbonate, or any combination thereof. Sensor 4 can detect an analyte concentration in a detection medium such as a biological sample. In some embodiments, sensor 4 is embedded in human tissue and comes in contact with a biological sample.

As used herein, the term "biological sample," refers to any suitable biological that comprises an electrolyte, a blood gas, or any other biological analyte. The biological sample may be obtained from a subject. A biological sample may be a fluid (e.g., a biological fluid). In general, a biological fluid can include any fluid associated with living organisms. Non-limiting examples of a biological sample include blood (or components of blood, e.g., white blood cells, red blood cells, and/or platelets) obtained from any anatomical location (e.g., tissue, circulatory system, bone marrow) of a subject, interstitial fluid, and saliva.

A biological sample may be obtained from a subject by any means known in the art. Non-limiting examples of means to obtain a biological sample directly from a subject include accessing the circulatory system (e.g., intravenously or intra-arterially via a syringe or other needle) and collecting a secreted biological sample (e.g., saliva or urine).

In some examples, the detection medium is blood. The blood can be venous blood and/or arterial blood. Sensor 4 can be exposed to the detection medium via a cardiopulmonary bypass circuit in which a pump is used to circulate and oxygenate blood extra-corporeally during certain surgical procedures such as, but not limited to coronary artery bypass surgery and cardiac valve repair and/or replacement. In some embodiments, the detection medium is saliva or urine.

Figure 2:
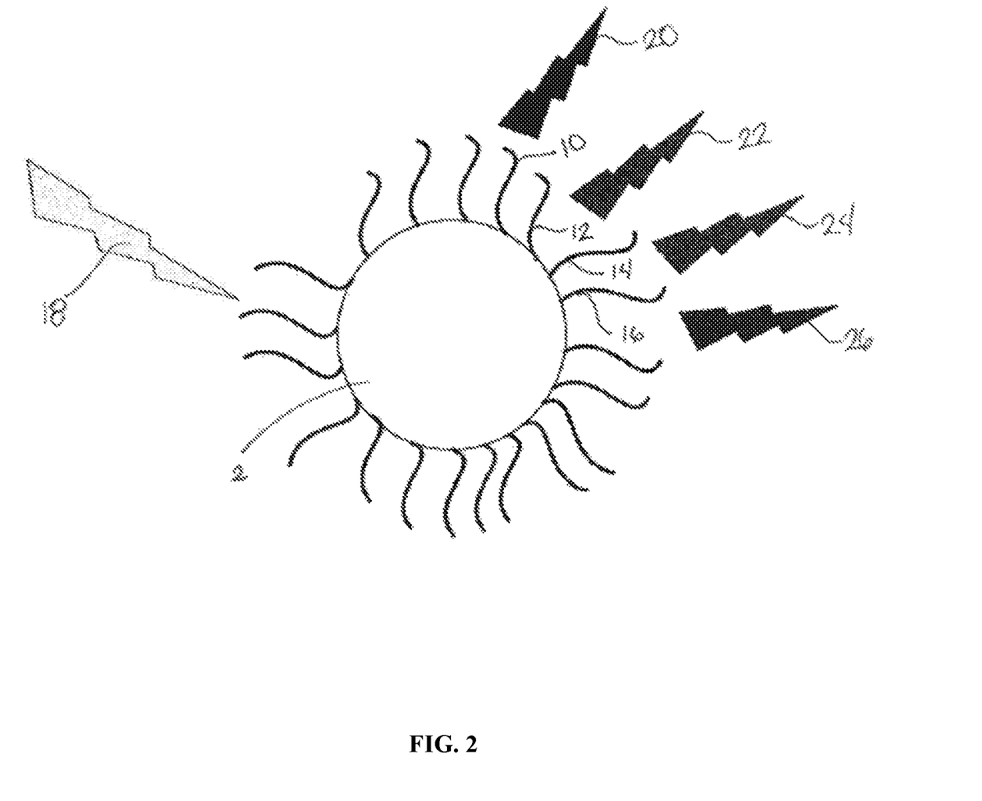
FIG. 2 is a schematically depicts an excitation process of a sensor in accordance with some embodiments provided herein.

Referring to FIG. 2, an example nanoparticle 2 for the detection of pH, oxygen, carbon dioxide, and potassium ions is schematically depicted. In this example, an excitation wavelength 18 is directed to nanoparticle 2. Excitation wavelength 18 excites a plurality of electrons of the pH-responsive signaling molecule 10, potassium-responsive signaling molecule 12, oxygen-responsive signaling molecule 14, and carbon dioxide-responsive signaling molecule 16. As a result, the signaling molecules emit light at distinguishable and distinct wavelengths as a function of a concentration of one or more analytes of interest. As shown in FIG. 2, pH-responsive signaling molecule 10 emits a pH-dependent emission wavelength 20. Potassium-responsive signaling molecule 12 emits a potassium-dependent emission wavelength 22. Oxygen-responsive signaling molecule 14 emits an oxygen-dependent emission wavelength 24. And carbon dioxide-responsive signaling molecule 16 emits a carbon dioxide-dependent emission wavelength 26. The pH-dependent emission wavelength 20, potassium-dependent emission wavelength 22, oxygen-dependent emission wavelength 24, and the carbon dioxide-dependent emission wavelength 26 can range from about 300 nanometers (nm) to about 900 nm.

Excitation wavelength 18 may originate from an energy source. The term "energy source," as used herein, generally refers to a source of energy providing a beam of energy. The energy source may provide a beam of electromagnetic energy or electromagnetic radiation. The energy source may provide a particle beam. An energy source may provide a light beam (e.g., gamma waves, x-ray, ultraviolet, visible light, infrared light, microwaves, or radio waves). The light beam may be a coherent light beam, as may be provided by light amplification by stimulated emission of radiation ("laser"). In some examples, the light beam is generated by a laser diode or a multiple diode laser. Excitation wavelength 18 can range from about 300 nanometers (nm) to about 900 nm.

The signaling molecule can be a fluorophore. Suitable pH-responsive signaling molecules 10 include pH indicators and/or functionalized derivatives of such indicators. The pH-responsive signaling molecule 10 can be hydroxypyrenetrisulfonic acid ("HPTS"), derivatives, e.g., salts, and/or mixtures thereof. In some embodiments, pH-responsive signaling molecule 10 is phenolphthalein, fluorescein, phenol red, cresol red, pararosaniline, magenta red, xylenol blue, bromocresol purple, bromophenol blue, bromothymol blue, metacresol purple, thymol blue, bromophenol blue, bromothymol blue, tetrabromophenol blue, bromochlorphenol blue, bromocresol green, chlorophenol red, o-cresolphthalein, thymolphthalein, metanil yellow diphenylamine, N,N-dimethylaniline, indigo blue, alizarin, alizarin yellow GG, alizarin yellow R, congo red, methyl red, methyl violet 6B, 2,5-dinitrophenol, and/or the various functionalized derivatives of the above species. Sensing components for other ionic species can be made from organic species including, but not limited to fluorescein, diiodofluorescein, dichlorofluorescein, phenosafrainin, rose bengal, eosin I bluish, eosin yellowish, magneson, tartrazine, eriochrome black T, coumarin, alizarin, and others.

Additional suitable pH-responsive signaling molecule components 10 for use with sensor 4 include, but are not limited to: 9-amino-6-chloro-2-methoxyacridine; 2',7'-bis-(2-carboxyethyl)-5-(and-6)-carboxyfluorescein; 2',7'-bis-(2-carboxyethyl)-5-(and-6)-carboxyfluorescein, acetoxymethyl ester; 2',7'-bis-(2-carboxyethyl)-5-(and-6)-carboxyfluorescein, acetoxymethyl ester; 5-(and-6)-carboxy-2',7'-dichlorofluorescein; 5-(and-6)-carboxy-2',7'-dichlorofluorescein diacetate; 5-(and-6)-carboxy-4',5'-dimethylfluorescein; 5-(and-6)-carboxy-4',5'-dimethylfluorescein diacetate; 5-carboxyfluorescein; 6-carboxyfluorescein; 5-(and-6)-carboxyfluorescein; 5-carboxyfluorescein diacetate; 6-carboxyfluorescein diacetate; 5-carboxyfluorescein diacetate, acetoxymethyl ester; 5-(and-6)-carboxyfluorescein diacetate; 5-(and-6)-carboxynaphthofluorescein; 5-(and-6)-carboxynaphthofluorescein diacetate; 5-(and-6)-carboxySNAFL®-1, succinimidyl ester {5'(and 6')-succinimidyl ester-3,10-dihydroxy-spiro[7H-benzo[c]xanthene-7,1'(3'H)-isobenzofuran]-3'-one}; 5-(and-6)-carboxySNAFL®-2, succinimidyl ester {5'(and 6')-succinimidyl ester-9-chloro-3,10-dihydroxy-spiro[7H-benzo[c]xanthene-7,1'(3'H)-isobenzofuran]-3'-one}; carboxySNAFL®-1 {5'(and 6')-carboxy-3,10-dihydroxy-spiro[7H-benzo[c]xanthene-7,1'(3'H)-isobenzofuran]-3'-one}; carboxySNAFL®-1 diacetate {5'(and 6')-carboxy-3,10-diacetoxy-spiro[7H-benzo[c]xanthene-7,1'(3'H)-isobenzofuran]-3'-one}; carboxySNAFL®-2 {5'(and 6')-carboxy-9-chloro-3,10-dihydroxy-spiro[7H-benzo[c]xanthene-7,1'(3'H)-isobenzofuran]-3'-one}; carboxySNAFL®-2 diacetate {5'(and 6')-carboxy-9-chloro-3,10-diacetoxy-spiro[7H-benzo[c]xanthene-7,1'(3'H)-isobenzofuran]-3'-one}; carboxySNARF®-1 {5'(and 6')-carboxy-10-dimethylamino-3-hydroxy-spiro[7H-benzo[c]xanthene-7,1 (3'H)-isobenzofuran]-3'-one}; carboxySNARF®-1, AM acetate (3-acetoxy-5'-acetoxymethoxycarbonyl-10-dimethylamino-spiro[7H-benzo[c]xanthene-7,1'(3'H)-isobenzofuran]-3'-one); carboxySNARF®-2 {5'(and 6')-carboxy-10-diethylamino-3-hydroxy-spiro[7H-benzo[c]xanthene-7,1'(3'H)-isobenzofuran]-3'-one}; carboxySNARF®-2, AM acetate {3-acetoxy-5'-acetoxymethoxycarbonyl-10-diethylamine-3-hydroxy-spiro[7H-benzo[c]xanthene-7,1'(3'H)-isobenzofuran]-3'-one}; carboxySNARF®-6 {5'(and 6')-carboxy-10-diethylamino-3-hydroxy-spiro[7H-benzo[c]xanthene-7,1'(3'H)-isobenzofuran]-3'-one}; carboxySNARF®-X {5'(and 6')-carboxy-3-hydroxy-tetrahydroquinolizino[1,9-hi]spiro[7H-benzo[c]xanthene-7,1'(3'H)-isobenzofuran]-3'-one}; 5-chloromethylfluorescein diacetate; 4-chloromethyl-7-hydroxycoumarin; C1-NERF {4-[2-chloro-6-(ethylamino)-7-methyl-3-oxo-3H-xanthen-9-yl]-1,3-benzene-dicarboxylic acid}; dextran, BCECF, 10,000 MW, anionic {dextran, 2',7'-bis(2-carboxyethyl)-5(and 6)-carboxy-fluorescein, anionic); dextran, BCECF, 40,000 MW, anionic; dextran, BCECF, 70,000 MW, anionic; dextran, C1-NERF, 10,000 MW, anionic; dextran, C1-NERF, 70,000 MW, anionic; dextran, C1-NERF, 10,000 MW, anionic, lysine fixable; dextran, DM-NERF, 10,000 MW, anionic (dextran, 4-[2,7-dimethyl-6-(ethylamino)-3-oxo-3H-xanthen-9-yl]-1,3-benzene dicarboxylic acid, anionic}; dextran, DM-NERF, 70,000 MW, anionic; dextran, DM-NERF, 10,000 MW, anionic, lysine fixable; dextran, 7-hydroxycoumarin, 10,000 MW, neutral; dextran, 7-hydroxycoumarin, 70,000 MW, neutral; dextran, b-methylumbelliferone, 10,000 MW, neutral; dextran, b-methylumbelliferone, 70,000 MW, neutral; dextran, SNAFL®-2, 10,000 MW, anionic {dextran, 9-chloro-3,10-dihydroxy-spiro[7H-benzo[c]xanthene-7,1' (3'H)-isobenzofuran]3'-one, anionic}; dextran, SNAFL®-2, 70,000 MW, anionic {dextran, 10-dimethylamino-3-hydroxy-spiro[7H-benzo[c]xanthene-7,1'(3'H)-isobenzofuran]-3'-one, anionic}; dextran, SNARF®-1, 10,000 MW, anionic; dextran, SNARF®-1, 70,000 MW, anionic; 1,4-dihydroxyphthalonitrile; DM-NERF {4-[2,7-dimethyl-6-ethylamino)-3-oxo-3H-xanthen-9-yl]1,3-benzene dicarboxylic acid}; fluorescein diacetate; 8-hydroxypyrene-1,3,6-trisulfonic acid, trisodium salt; naphthofluorescein; naphthofluorescein diacetate; SNAFL®-1 {3,10-dihydroxy-spiro[7H-benzo[c]xanthene-7,1'(3'H)-isobenzofuran]-3'-one); and SNAFL®-1, diacetate (3,10-diacetoxy-spiro[7H-benzo[c]xanthene-7,1'(3'H)-isobenzofuran]-3'-one}.

The potassium-responsive signaling molecule 12 can be a coumarocryptand; for example, 6,7-[2.2.2]-cryptando-3-[2"-(5"-carboxy)furyl]coumarin. In some cases, the potassium-responsive signaling molecule 12 contains a complexing moiety for binding an ion and a fluorescing moiety. The compound has a wavelength of maximum absorbance of at least about 350 nm. Suitable fluorescing moieties may contain close-lying $n\pi^*$ and $\pi\pi^*$ excited states. Suitable fluorescing moieties, when coupled to an appropriate complexing moiety, can be capable of ion dependent out-of-plane puckering. Also, the $\pi\pi^*$ state of suitable fluorescing moieties can be sufficiently high in energy that ion dependent mixing dominates non-radiative coupling to the ground state. In some instances, fluorescing moieties include coumarin moieties, although other aromatic carbonyls or nitroaromatics or N-heterocyclic moieties may be employed. Suitable ion complexing moieties include cyclic "cage" moieties capable of binding an ion. The cage may be capable of selective binding of an ion. In some examples, ion complexing moieties include cryptand and crown ether moieties.

Ions which may be sensed using the ionophore include, for example, $Ag^+$, $Ba^+$, $Ca^{2+}$, $Ce^+$, $Cd^{2+}$, $Fr^+$, $Hg^{2+}$, $K^+$, $Li^+$, $Mg^{2+}$, $Na^+$, $Pb^{2+}$, $Ru^+$, $Sr^+$, $Ti^+$, and $Zn^{2+}$. If desired the ionophore may be used in conjunction with an ion selective membrane. In some examples, the sensors provided herein comprise ionophores that sense for $K^+$, $Na^+$, and $Ca^{2+}$.

In some embodiments, the oxygen-responsive signaling molecule 14 is benzo[ghi]perylene. The oxygen-responsive signaling molecule 14 may comprise fluorescence indicators including one or more polynuclear aromatic compounds, derivatives of polynuclear aromatic compounds and the like. Examples of such polynuclear aromatic compounds include decacyclene, benzo[ghi]perylene, and coronene. Oxygen indicators may include a mixture of tertiary butyl derivatives of such polynuclear aromatic compounds.

Additional useful oxygen indicators include complexes of ruthenium(II), osmium(II), iridium(III), rhodium, rhenium, and chromium(III) with 2,2'bipyridine, 1,10-phenanthroline, 4,7-diphenyl-1,10-phenanthroline, 4,7-dimethyl-1,10-phenanthroline, 4,7-disulfonated-diphenyl-1,10-phenanthroline, 2,2'bi-2-thiazoline, 2,2'bithiazole, 5-bromo-1,10-phenanthroline, and 5-chloro-1,10-phenthroline, and complexes of Co(II), Cu(II), Pt(II), Pd(II) and Zn(II) with porphyrin, etioporphyrin, tetraphenylporphorin, tetrafluorophenylporphirin, tetrabenzporphirin, tetrafluorobenzporphirin, tetrachlorobenzporphirin, mesoporphirin IX diester, protoporphirin IX dimethyl ester, and octaethylporphorin. Ruthenium complexes, among the metal complexes.

In some embodiments, the oxygen-responsive signaling molecule 14 is sensitive to the concentration of oxygen in a fluid and comprises one or more polynuclear aromatic compounds and/or one or more derivatives thereof. The polynuclear aromatic compound can be any fluorescent or absorbent optical indicator of the polynuclear aromatic class. The polynuclear aromatic compound from which the indicator component is derived may be selected from the group consisting of perylene, decacyclene, benzoperylene (e.g., benzo[ghi]perylene), coronene, pyrene, porphycine, porphyrin, chlorin, phthalocyanine and derivatives and mixtures thereof. Since perylene and derivatives of perylene have a relatively reduced sensitivity to oxygen, other polynuclear aromatic compounds, such as those noted herein, can be employed when the analyte is oxygen. When an excimer component is to be utilized, the monomeric indicator component may be selected from one polynuclear aromatic compound, derivatives of the same one polynuclear aromatic compound and mixtures thereof.

In some instances, carbon dioxide-responsive signaling molecule 16 comprises a hydroxypyrene 3,6,8-trisulfonic acid, herein referred to as HPTS or hydroxypyrene trisulfonic acid and derivatives, e.g., salts of HPTS. Alkali and alkaline earth metal salts of HPTS can be used by sensors disclosed herein to detect carbon dioxide concentration in a fluid. The carbon dioxide-responsive signaling molecule 16 can be an absorbance or a fluorescence indicator. In sensing carbon dioxide concentrations, examples of absorbance indicators that can be used include chlorophenyl red, bromo cresol purple, nitrophenol, bromo thymol blue, penachlorome, phenol red, and the like. Useful fluorescence indicators for carbon dioxide include the sensors listed above that are useful for pH sensing, beta-methylumbelliferone, fluorescein, and the like.

In some embodiments, sensor 4 is a fluorescence resonance energy transfer (FRET)-based sensor. FRET is a mechanism in which there is an energy transfer between two light-sensitive molecules (i.e., chromophores) that are in close proximity to each other, without emission of a photon. A donor chromophore, initially in its electronic excited state, may transfer energy to an acceptor chromophore through non-radiative dipole-dipole coupling. The efficiency of this energy transfer is inversely proportional to the sixth power of the distance between the donor chromophore and the acceptor chromophore, making FRET extremely sensitive to small changes in distance. Sensor 4 can comprise a donor chromophore and an acceptor chromophore. The donor chromophore can transfer energy to the acceptor chromophore in the presence of the analyte, causing the acceptor chromophore to exhibit a distinguishable emission wavelength indicative of the presence of the analyte. In some embodiments, the donor chromophore and/or the acceptor chromophore is a nanoparticle (e.g., a quantum dot or a polymeric nanoparticle). In other examples, the donor chromophore and/or the acceptor chromophore is a fluorescent dye or protein. In yet another example, both the donor chromophore and the acceptor chromophore are fluorescent dyes or proteins. Non-limiting examples of fluorescent dyes or proteins used in FRET include cyan fluorescent protein (CFP), yellow fluorescent protein (YFP), green fluorescent protein (GFP), fluorescein, BODIPY FL, tetramethylrhodamine, 5-({2-[(iodoacetyl)amino]ethyl}amino)naphthalene-1-sulfonic acid (IAEDANS), Alexa Fluor 488, Oregon Green, (5-((2-Aminoethyl)amino)naphthalene-1-sulfonic acid) (EDANS), 4-(dimethylaminoazo)benzene-4-carboxylic acid (DABCYL), 4-(4-dimethylaminophenylazo)benzenesulfonyl chloride (DABSYL), QSY®7, QSY®9, cyanine3 (Cy3), Cy3.5, Cy5.5, Cy7, or any combination thereof.

In some examples, the donor chromophore is a quantum dot and the acceptor chromophore is a fluorescent dye. In some cases, the donor chromophore is a nanoparticle and the acceptor chromophore is a fluorescent dye. In some examples, the fluorescent dye is a ratiometric dye. In some embodiments, the fluorescent dye is Cy5.5. In some implementations, the sensor is a nanoparticle having a donor quantum dot core and a fluorescent dye acceptor coating. For example, the nanoparticle may have a quantum dot core and a lipid coating, which includes a fluorescent dye (e.g., Cy5.5). In some embodiments, the donor chromophore is a fluorescent dye and the acceptor chromophore is a quantum dot or a polymeric nanoparticle.

The sensors of the disclosure may be modified with "sequestering" molecules that bind interferents and reduce their impact on accuracy. As an example, a sodium binding cryptand can be immobilized on the surface of a potassium-specific sensor to reduce its availability to interfere with potassium detection. In one embodiment, the binding of sodium may be non-fluorescent and solely be present to reduce interference. In another example, the nanomaterial may bind sodium and provide a concentration dependent response such that the interference on potassium accuracy is reduced and the sensor reports on the concentration of sodium.

In some embodiments, the sensor is a temperature-sensitive sensor. In some embodiments, the sensor may include a temperature sensitive channel, such that the output signal (e.g., a fluorescence emission intensity or a ratio of two fluorescence emission intensities) of the sensor responds to a change in temperature. In some examples, such temperature-dependent signal can be used as a reference for temperature correction. In some embodiments, the sensor comprises a nanoparticle or a signaling molecule exhibiting a fluorescence emission intensity as a function of a temperature (e.g., a temperature of a sample). In some embodiments, the sensor comprises a donor chromophore transferring energy to an acceptor chromophore as function of a temperature, causing the acceptor chromophore to exhibit a distinguishable emission wavelength indicative of a temperature change (e.g., a change in temperature of a sample). For example, the sensor may comprise a quantum dot that exhibits temperature-sensitive photoluminescence.

In an aspect, the present disclosure provides a method of detecting an analyte concentration in a fluid. The method may comprise providing one or more sensors comprising a matrix material, a nanoparticle associated with the matrix material, and a signaling molecule associated with the nanoparticle. The signaling molecule or the nanoparticle exhibit a fluorescence emission intensity that depends on the analyte concentration. Next, the method may comprise exposing the one or more sensors to the fluid. For example, the one or more sensors may be part of a cardiopulmonary bypass circuit via placement along tubing in fluid connection with blood from a patient. In another example, the one or more sensors may be connected to a flow-through cell that has fittings on opposite sides for coupling to the circuit tubing.

Next, the method may comprise measuring the fluorescence emission intensity. The sensor can be optically coupled to a measuring device that outputs a measured fluorescence emission intensity. The sensor can be remotely coupled to the measuring device. In other words, the measuring device can be a remote measuring device. The measuring device may be a blood gas measuring device. The measuring device can include: an energy source for directing light to the one or more sensors, an apparatus for analyzing the light returned from the one or more sensors, and a monitor for providing a visual display of the measurement. In some examples, the measuring device can comprise a bundle of optical fibers extending from the remote device to a transmission block or retainer and a releasable coupling provided to detachably connect the retainer or block to a cell or housing that supports the sensors.

Next, the method may comprise detecting the analyte based on the measured fluorescence intensity. Once light from an energy source is directed to the one or more sensors, the light emitted from the one or more sensors is detected. The emitted light from the one or more sensors may be detected by a detector (e.g., a photodiode). The detector may then send the light signal to a converter that converts the emitted light to a digital signal. In another example, the detector may send the light signal to an amplifier that amplifies the light signal before transmitting it to the converter. After the emitted light has been converted to a digital signal, the controller can send the digital signal to a controller and/or the monitor. The controller can be operatively connected to the monitor and energy source. The controller can receive instructions from the monitor. The transmitted digital signal can be one or more measured fluorescence intensity values.

While a number of examples have been described for illustration purposes, the foregoing description is not intended to limit the scope of the invention, which is defined by the scope of the appended claims. There are and will be other examples and modifications within the scope of the following claims.

What is claimed is:

1. A sensor for detecting a concentration of analytes, the sensor comprising:
   a matrix material;
   a nanoparticle associated with the matrix material; and
   a plurality of signaling molecules coupled to the nanoparticle, the plurality of signaling molecules comprising hydroxypyrenetrisulfonic acid (HPTS), benzo[ghi]perylene, and a coumarocryptand,
   wherein the nanoparticle or the plurality of signaling molecules exhibit a fluorescence emission intensity as a function of the concentration of each of the analytes,
   wherein the analytes comprise potassium, oxygen, carbon dioxide, and hydrogen ions,
   wherein the HPTS configures the sensor to detect the concentration of hydrogen ions and carbon dioxide, the benzo(ghi)perylene configures the sensor to detect the concentration of oxygen, and the coumarocryptand configures the sensor to detect the concentration of potassium, and
   wherein the nanoparticle is formulated such that each signaling molecule of the plurality of signaling molecules is responsive to a same single excitation wavelength, causing an emission of independent fluorescence emission intensities for each of the potassium, oxygen, carbon dioxide, and hydrogen ions.

2. The sensor of claim 1, wherein the matrix material is a hydrogel matrix.

3. The sensor of claim 1, wherein the matrix material is permeable to the one or more analytes.

4. The sensor of claim 1, wherein the nanoparticle is a polymeric nanoparticle.

5. The sensor of claim 1, wherein the nanoparticle is a quantum dot.

6. The sensor of claim 5, wherein the quantum dot exhibits a distinguishable emission wavelength.

7. The sensor of claim 5, wherein the signaling molecule alters a fluorescence emission intensity of the quantum dot as a function of the concentration of the one or more analytes.

8. The sensor of claim 1, wherein the plurality of signaling molecules decreases or increases the fluorescence emission intensity of the nanoparticle in the absence of the one or more analytes.

9. The sensor of claim 1, wherein the plurality of signaling molecules increases or decreases the fluorescence emission intensity of the nanoparticle in the presence of the one or more analytes.

10. The sensor of claim 1, wherein the sensor is optically coupled to a measuring device.

11. The sensor of claim 1, wherein the sensor is a ratiometric sensor.

12. The sensor of claim 1, wherein the nanoparticle or the plurality of signaling molecules exhibit a fluorescence emission intensity as a function of a temperature.

13. A sensor for detecting a concentration of analytes, the sensor comprising:
    a matrix material;
    a donor chromophore; and
    a plurality of acceptor chromophores,
    wherein the donor chromophore transfers energy to the plurality of acceptor chromophores in the presence of the analytes, causing the plurality of acceptor chromophores to exhibit independent emission wavelengths indicative of the presence of each analyte, and
    wherein the analytes comprise potassium, oxygen, carbon dioxide, and hydrogen ions,
    wherein the donor chromophore or the acceptor chromophore comprises hydroxypyrenetrisulfonic acid (HPTS), benzo[ghi]perylene, and a coumarocryptand,
    wherein the HPTS configures the sensor to detect the concentration of hydrogen ions and carbon dioxide, the benzo(ghi)perylene configures the sensor to detect the concentration of oxygen, and the coumarocryptand configures the sensor to detect the concentration of potassium, and
    wherein the sensor is formulated such that each acceptor chromophore of the plurality of acceptor chromophores is responsive to a same donor chromophore, causing an emission of independent emission wavelengths for each of the potassium, oxygen, carbon dioxide, and hydrogen ions.

14. The sensor of claim 13, wherein the matrix material is a hydrogel matrix.

15. The sensor of claim 13, wherein the matrix material is permeable to the analyte.

16. The sensor of claim 13, wherein the donor chromophore or the acceptor chromophore is a nanoparticle.

17. The sensor of claim 16, wherein the nanoparticle is a polymeric nanoparticle.

18. The sensor of claim 16, wherein the nanoparticle is a quantum dot.

19. The sensor of claim 13, wherein the acceptor chromophore or the donor chromophore is a fluorescent dye.

20. The sensor of claim 13, wherein the sensor is optically coupled to a measuring device.

21. The sensor of claim 13, wherein the sensor is a ratiometric sensor.

22. The sensor of claim 13, wherein the donor chromophore transfers energy to the acceptor chromophore as a function of a temperature, causing the acceptor chromophore to exhibit a distinguishable emission wavelength indicative of a temperature change.

23. A method of detecting a concentration of one or more analytes in a fluid, the method comprising:
providing one or more sensors comprising:
a matrix material;
a nanoparticle associated with the matrix material; and
a plurality of signaling molecules coupled to the nanoparticle, the plurality of signaling molecules comprising hydroxypyrenetrisulfonic acid (HPTS), benzo[ghi]perylene, and a coumarocryptand,
wherein the one or more analytes comprises potassium, oxygen, carbon dioxide, and hydrogen ions,
wherein the nanoparticle is formulated such that each signaling molecule of the plurality of signaling molecules is responsive to a same single excitation wavelength, causing an emission of independent fluorescence emission intensities for each of the potassium, oxygen, carbon dioxide, and hydrogen ions, and
wherein the nanoparticle or the plurality of signaling molecules exhibit a fluorescence emission intensity as a function of the concentration of the one or more analytes;
exposing the one or more sensors to the fluid;
exposing the one or more sensors to the same excitation wavelength;
measuring the independent fluorescence emission intensities for each of the analytes; and
detecting the one or more analytes based on the measured fluorescence intensity,
wherein the HPTS configures the sensor to detect the concentration of hydrogen ions and carbon dioxide, the benzo(ghi)perylene configures the sensor to detect the concentration of oxygen, and the coumarocryptand configures the sensor to detect the concentration of potassium.

24. The method of claim 23, wherein the fluid is a biological fluid.

25. The method of claim 24, wherein the biological fluid is blood.

* * * * *